US012758110B2

(12) United States Patent
Moriyama et al.

(10) Patent No.: US 12,758,110 B2
(45) Date of Patent: Oct. 13, 2026

(54) DYNAMIC MULTI-DEVICE PHYSIOLOGICAL MEASUREMENT SYSTEMS AND METHODS

(71) Applicant: Apple Inc., Cupertino, CA (US)

(72) Inventors: Ryan M. Moriyama, Santa Monica, CA (US); Soroush Massoumi, Playa Del Rey, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 19/267,320

(22) Filed: Jul. 11, 2025

(65) Prior Publication Data

US 2026/0033732 A1 Feb. 5, 2026

Related U.S. Application Data

(60) Provisional application No. 63/677,530, filed on Jul. 31, 2024.

(51) Int. Cl.

| | |
|---|---|
| ***A61B 5/00*** | (2006.01) |
| ***A61B 5/0205*** | (2006.01) |
| ***A61B 5/024*** | (2006.01) |
| ***A61B 5/0255*** | (2006.01) |
| ***A61B 5/11*** | (2006.01) |

(52) U.S. Cl.

CPC .......... *A61B 5/0255* (2013.01); *A61B 5/0205* (2013.01); *A61B 5/02416* (2013.01); *A61B 5/02438* (2013.01); *A61B 5/11* (2013.01); *A61B 5/7271* (2013.01); *A61B 2560/0462* (2013.01); *A61B 2562/0219* (2013.01)

(58) Field of Classification Search

CPC .................................................... A61B 5/0255

See application file for complete search history.

(56) References Cited

U.S. PATENT DOCUMENTS

| | | | |
|---|---|---|---|
| 9,655,532 | B2 | 5/2017 | Blake et al. |
| 10,271,727 | B2 | 4/2019 | Marcus et al. |
| 11,020,001 | B2 | 6/2021 | Melodia et al. |
| 11,883,197 | B1 | 1/2024 | Lisy et al. |
| 2017/0296070 | A1 | 10/2017 | Wegerich et al. |

FOREIGN PATENT DOCUMENTS

| | | | |
|---|---|---|---|
| CN | 204562150 | U | 8/2015 |
| CN | 105996990 | A | 10/2016 |
| CN | 115736871 | A | 3/2023 |
| DE | 102017112855 | A1 | 12/2018 |
| WO | WO 2016110804 | A1 | 7/2016 |

*Primary Examiner* — Joseph M Santos Rodriguez

(74) *Attorney, Agent, or Firm* — Brownstein Hyatt Farber Schreck, LLP

(57) ABSTRACT

Embodiments include systems and methods for determining a physiological value of a user. The systems and methods described herein may be configured to select and obtain physiological metrics from multiple electronic devices in order to generate an output physiological value for a measured physiological parameter. In some cases, an electronic device is configured to receive physiological metrics from one or more other electronic devices and generate the output physiological value using one or more of the received physiological metrics. Additionally, in some cases, the electronic device may be configured to generate a physiological metric (e.g., using a physiological sensor incorporated in the electronic device), and may use both the generated physiological metric and the one or more received physiological metrics in generating the output physiological value.

20 Claims, 5 Drawing Sheets

DYNAMIC MULTI-DEVICE PHYSIOLOGICAL MEASUREMENT SYSTEMS AND METHODS

CROSS REFERENCE TO RELATED APPLICATION

This application is a nonprovisional and claims the benefit under 35 U.S.C. § 119(e) of U.S. Provisional Patent Application No. 63/677,530, filed Jul. 31, 2024, the contents of which are incorporated herein by reference as if fully disclosed herein.

FIELD

The described embodiments relate generally to systems and methods for measuring physiological parameters of a user using multiple devices. More particularly, the present embodiments relate to systems and methods that determine a physiological value using physiological metrics that are measured by multiple devices.

BACKGROUND

Electronic devices such as smartwatches, ear-worn devices, and smartphones are increasingly incorporating sensing systems that measure physiological parameters of a user. In many cases a user may have multiple devices that independently measure the same physiological parameter. Due to difference in the sensing location and/or the sensing systems of the different devices, each device may output different values of a physiological parameter for the same period of time. For example, if two different devices are measuring a heart rate of a user, each of the devices may output a different heart rate based on a variety of factors that may impact the individual measurements performed by these devices. This may negatively impact a user's experience, as they may be uncertain of which measurement best represents the user's current state.

SUMMARY

Embodiments are directed to systems and methods for determining a physiological value of a physiological parameter of a user. In some instances, a system includes a first wearable electronic device having a first heart rate sensor and a first wireless communication device, where the first wearable electronic device configured to operate the first heart rate sensor to detect a first heart rate metric at a first location on the user. The system may include a second wearable electronic device that includes a second heart rate sensor and a second wireless communication device. The second wearable electronic device may be configured to i) operate the second heart rate sensor to detect a second heart rate metric at a second location on the user, and ii) operate the second wireless communication device to transmit the second heart rate metric to the first wearable electronic device. The system may include a third wearable electronic device that includes a third heart rate sensor and a third wireless communication device, where the third wearable electronic device configured to operate the third heart rate sensor to detect a third heart rate metric at a third location on the user. In some variations, the first heart rate sensor, the second heart rate sensor and the third heart rate sensor each include an optical sensor.

The first wearable electronic device may be configured to i) compare the first heart rate metric to the second heart rate metric for a first measurement window, and ii) operate the first wireless communication device to transmit, for the first measurement window, one of the first heart rate metric or the second heart rate metric to the third wearable electronic device based on the comparison. The third wearable electronic device may be configured to use the received one of the first heart rate metric or the second heart rate metric, and the third heart rate metric, to generate a heart rate value for the user for the first measurement window. The third wearable electronic device may cause the generated heart rate value to be output to the user.

In some variations, comparing, by the first wearable electronic device, the first heart rate metric to the second heart rate metric includes comparing a first confidence metric associated with the first heart rate metric to a second confidence metric associated with the second heart rate metric. In these variations, the first wearable electronic device may select the one of the first heart rate metric or the second heart rate metric associated with a greater confidence metric for transmitting to the third wearable electronic device. In some variations, in response to the third wearable electronic device selecting the received one of the first heart rate metric or the second heart rate metric to generate the heart rate value, the third wearable electronic device is configured to deactivate the third heart rate sensor.

Additionally or alternatively, the third wearable electronic device may be configured to monitor a confidence metric associated with the received one of the first heart rate metric or the second heart rate metric, and, in response to the confidence metric falling below a confidence threshold: i) cause the first wearable electronic device to compare, for a second measurement window, the first heart rate metric to the second heart rate metric, and ii) transmit one of the first heart rate metric or the second heart rate metric for the second measurement window to the third wearable electronic device based on the comparison for the second measurement window. In some variations, the first wearable electronic device is configured to compare the first heart rate metric to the second heart rate metric at a defined interval, and for each comparison at the defined interval, select the one of the first heart rate metric or the second heart rate metric to transmit to the third wearable electronic device. For example, a defined interval may include one or more measurement periods, and the selected one of the first heart rate metric or the second heart rate metric may be transmitted to third wearable electronic device for each measurement period within the defined interval.

In some variations, the third wearable electronic device includes a motion sensor configured to detect motion and generate a motion signal. The third wearable electronic device may be configured to select the received one of the first heart rate metric or the second heart rate metric or the third heart rate metric to generate the heart rate value based on the motion signal. In some of these variations, the third wearable electronic device is configured to i) determine an activity of the user using the motion signal and ii) select the received one of the first heart rate metric or the second heart rate metric, or the third heart rate metric to generate the heart rate value based on the determined activity. Additionally or alternatively, the third wearable electronic device is configured to generate the heart rate value by applying a weight parameter to the third heart rate metric, the weight parameter determined using a corresponding confidence metric. In other variations, the third wearable electronic device is configured to generate the heart rate value by i) applying a first weight parameter to the received one of the first heart rate metric and the second heart rate metric, the first weight parameter determined using a first confidence metric determined for the received one of the first heart rate metric and the second heart rate metric, and ii) applying a second weight parameter to the third heart rate metric, the second weight parameter determined using a second confidence metric determined for the third heart rate metric.

In some instances, a system includes a first wearable electronic device that includes a first heart rate sensor and a first wireless communication device, where the first wearable electronic device is configured to operate the first heart rate sensor to determine a first heart rate metric at a first location on the user. The system may include a second wearable electronic device that a second heart rate sensor and a second wireless communication device, where the second wearable electronic device configured to operate the second heart rate sensor to determine a second heart rate metric at a second location on the user. The system may also include a third wearable electronic device that includes a third heart rate sensor and a third wireless communication device. The third wearable electronic device may be configured to operate the third heart rate sensor to determine a third heart rate metric at a third location on the user and receive at least one of the first heart rate metric and the second heart rate metric. In some variations, each of the first heart rate sensor, the second heart rate sensor and the third heart rate sensor includes an optical sensor.

The third wearable electronic device may be configured to determine, for a first measurement window, a first heart rate value for the user using the received one of the first and second heart rate metrics, the third hear rate metric, and a first set of weight parameters. The first set of weight parameters determined using first confidence metrics for each of the first heart rate metric, the second heart rate metric and the third heart rate metric. The third wearable device may also be configured to determine, for a second measurement window, a second heart rate value for the user using the received of the first and second heart rate metrics, the third heart rate metric and a second set of weight parameters. The second set of weight parameters may be determined using second confidence metrics for each of the first heart rate metrics, the second heart rate metrics and the third heart rate metrics.

In some of these variations, the third wearable electronic device is configured to, in response to determining that a confidence metric associated with the third heart rate metric fails to satisfy a criteria: deactivate the third heart rate sensor for the first measurement window, and determine the first heart rate value using the first heart rate metric and the second heart rate metric. In some variations, the first wearable electronic device is configured to, for each of the first measurement window and the second measurement window: i) receive the second heart rate metric from the second wearable electronic device, ii) compare the first heart rate metric to the second heart rate metric, and iii) operate the first wireless communication device to transmit one of the first heart rate metric or the second heart rate metric to the third wearable electronic device based on the comparison. In some of these variations, the third wearable electronic device is configured to determine the first and second heart rate values using the received one of the first heart rate metric and the second heart rate metric and the third heart rate metric for each respective measurement window. Additionally or alternatively, the first wearable electronic device is configured to, for each of the first measurement window and the second measurement window: i) in response to transmitting the first heart rate metric to the third wearable electronic device, deactivate the second heart rate sensor for a subsequent measurement window; and ii) in response to transmitting the second heart rate metric to the third wearable electronic device, deactivate the first heart rate sensor for a subsequent measurement window.

Still other variations are directed to a system that includes a first wearable electronic device that a first heart rate sensor and a first wireless communication device, where the first wearable electronic device configured to operate the first heart rate sensor to detect a first heart rate metric at a first location on the user. The system includes a second wearable electronic device that includes a second heart rate sensor and a second wireless communication device, where the second wearable electronic device configured to operate the second heart rate sensor to detect a second heart rate metric at a second location on the user. The system includes a third wearable electronic device that includes a third heart rate sensor and a third wireless communication device, where the third wearable electronic device configured to operate the third heart rate sensor to detect a third heart rate metric at a third location on the user.

The system further includes an electronic device, such that for a first measurement window: i) the first wearable electronic device is configured to select one of the first heart rate metric or the second heart rate metric to transmit to the electronic device based on a first comparison of confidence metrics of the first and second heart rate metrics, and ii) the electronic device is configured to use the received one of the first heart rate metric or the second heart rate metric, and the third heart rate metric, to generate a first heart rate value for the user for the first measurement window. For a second measurement window: i) the first wearable electronic device is configured to select one of the first heart rate metric or the second heart rate metric to transmit to the electronic device based on a second comparison of the confidence metrics of the first and second heart rate metrics, and ii) the electronic device is configured to use the received one of the first heart rate metric or the second heart rate metric, and the third heart rate metric, to generate a second heart rate value for the user for the second measurement window.

In some of these variations, the first comparison of the confidence metrics of the first and second heart rate metrics precedes the first measurement window. Additionally or alternatively, the second comparison of the confidence metrics of the first and second heart rate metrics may precede the second measurement window. In some of these variations, in response to selecting the first heart rate metric to transmit to the electronic device for the second measurement window, the first wearable electronic device is configured to cause the second heart rate sensor to deactivate for at least a portion of the second measurement window. In other variations, in response to determining that a confidence metric associated with the third heart rate metric falls below a defined threshold for the second measurement window, the third wearable electronic device is configured to deactivate the third heart rate sensor for at least a portion of a third measurement window. In some of these variations, the electronic device is configured to determine a third heart rate value for the third measurement window using the first heart rate metric or the second heart rate metric selected for the third measurement window.

BRIEF DESCRIPTION OF THE DRAWINGS

The disclosure will be readily understood by the following detailed description in conjunction with the accompanying drawings, wherein like reference numerals designate like structural elements, and in which.

Figure 1:
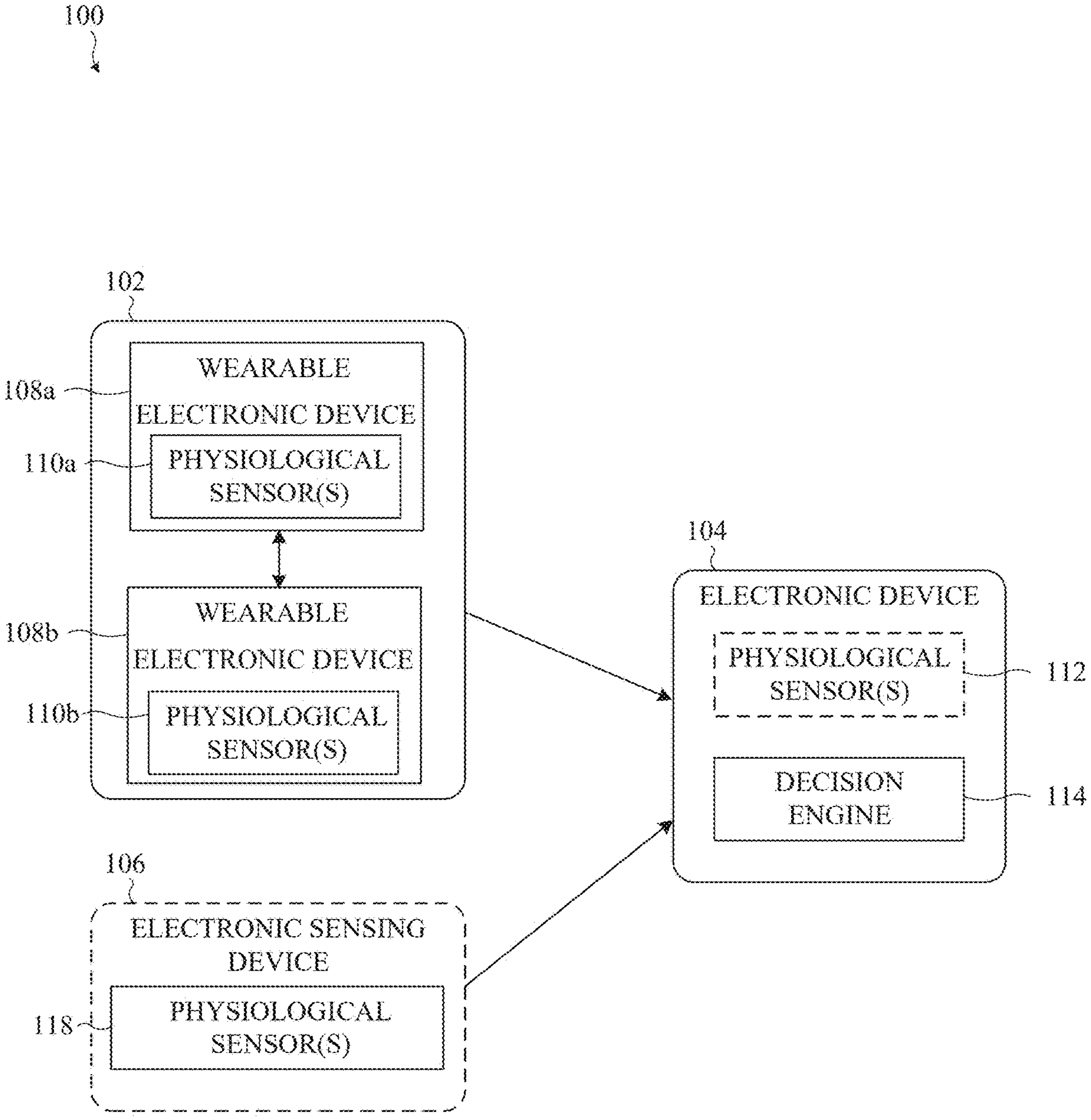
FIG. 1 shows a system that includes multiple electronic devices that can be used to determine a physiological parameter of a user.

It should be understood that the proportions and dimensions (either relative or absolute) of the various features and elements (and collections and groupings thereof) and the boundaries, separations, and positional relationships presented there between, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are directed to devices, systems, and methods for generating a value of a physiological parameter using measured physiological metrics from multiple electronic devices. As used herein, a "physiological parameter" refers to a parameter that can be measured from a user and that indicates an aspect of the user's health or wellbeing. Examples of physiological parameters include, but are not limited to, heart rate, heart rate variability, blood oxygen saturation, and respiration rate. A measurement of a physiological parameter may be represented by a value (also referred to herein as a "physiological value") for a given segment of time (also referred to herein as a "measurement period"). For example, a user's heart rate over a measurement period may be represented by a number of beats per minute. Similarly, heart rate variability may be measured in milliseconds, blood oxygen saturation may be measured as a percentage that represents the proportion of hemoglobin molecules in the user's blood that are carrying oxygen, and respiration rate may be measured in breaths per minute. When a particular physiological parameter is measured by a device over time, the device may generate multiple physiological values, each corresponding to a different measurement period.

In some instances, a user may simultaneously use multiple devices that are each capable of independently measuring the same physiological parameter. For a single measurement period, these devices may collectively generate multiple physiological values that may vary between devices. For example, if a user is wearing both i) a first device, such as a smartwatch, that has a first heart rate sensor (e.g., a sensor that is configured to measure heart rate) and ii) a second device, such as an earpiece, headphone, or other head-mounted device, that has a second heart rate sensor, it is possible that the these devices may output different heart rate values for a given period of time. In a non-limiting example, the first device may measure a heart rate of 85 beats per minute for a given measurement period and the second device may measure a heart rate of 95 beats per minute for the same measurement period. While this difference may depend on a number of factors (the configurations of the different sensors, the relative motion between the user and each device, etc.), a user may not readily know which physiological value is more reliable.

Accordingly, the devices, systems, and methods described here may use information from multiple devices to generate a single value of a physiological parameter for a given measurement period (also referred to herein as the "output physiological value" of the physiological parameter). Specifically, a decision engine as described herein receives multiple physiological metrics from multiple devices (which may include the device that incorporates the decision engine) for a given measurement period and may generate an output physiological value using the multiple physiological metrics. As used herein, a "physiological metric" refers to data corresponding to a particular measurement period that includes a physiological value and/or may be used to determine a physiological value for the measurement period. In some variations the physiological metric may include a physiological value that was calculated by a corresponding device during the measurement period. Additionally or alternatively, the physiological metric may include sensor data collected by the corresponding device that may be used to derive a physiological value for the measurement period. The sensor data may be raw sensor data or may be partially processed sensor data.

Using heart rate as an example, each device may be configured to generate a heart rate metric (e.g., the physiological metric for heart rate) for a given measurement period. In some instances, the heart rate metric may include a heart rate value calculated by a corresponding device. For example, a first device may generate a first heart rate metric that includes a first heart rate value (e.g., 85 beats per minute) for a measurement period, a second device may generate a second heart rate metric that includes a second heart rate value (e.g., 90 beats per minute) for the measurement period, and so on. In other instances, the heart rate metric may include sensor data generated from a corresponding heart rate sensor. For example, in instances where a heart rate sensor of a given device is an optical sensor, the heart rate metric may include individual intensity values that are measured by a detector of the optical sensor over the measurement window. Additionally or alternatively, the raw sensor data may be partially processed to identify individual heartbeats within the measurement window, and the heart rate metric may include timing information about the identified heartbeats. While the heart rate metric may include a range of possible information, in some instances it may be preferable to limit the heart rate metric to a heart rate value to reduce power consumption associated with transmitting the heart rate metrics between devices and processing the heart rate metrics to generate an output heart rate value.

While the various embodiments described herein are discussed with respect to the example of heart rate as a physiological parameter (e.g., using heart rate metrics from multiple devices to generate an output heart rate value), these teachings may additionally or alternatively be applied to other physiological parameters, such as heart rate variability, blood oxygen saturation, and/or respiration rate. For any given physiological parameter, a decision engine may obtain corresponding physiological metrics associated with that physiological parameter (e.g., heart rate variability metrics for heart rate variability, blood oxygen saturation metrics for blood oxygen saturation, and so on) from multiple devices, and may generate an output physiological value (e.g., an output heart rate variability value, an output blood oxygen saturation value, and so on) using the corresponding physiological metrics.

Accordingly, the systems and methods described herein are configured to select and obtain physiological metrics from multiple electronic devices in order to generate an output physiological value for a measured physiological parameter. In some cases, an electronic device is configured to receive physiological metrics from one or more other electronic devices and generate the output physiological value using one or more of the received physiological metrics. Additionally, in some cases, the electronic device may be configured to generate a physiological metric (e.g., using a physiological sensor incorporated in the electronic device), and may use both the generated physiological metric and the one or more received physiological metrics in generating the output physiological value.

Specifically, a decision engine may obtain a plurality of physiological metrics for a given measurement period (e.g., generated by an electronic device that incorporates the decision engine and/or received from other electronic devices), and may use the obtained physiological metrics to generate an output physiological value for the measurement period. An electronic device of the systems and methods described herein incorporates the decision engine and may include a memory and a processor operatively coupled to the memory. The processors are configured to execute instructions, which are stored in the memory causing the processor to perform the various operations of the decision engine.

In some variations, in addition to obtaining a plurality of physiological metrics for a given measurement period, the decision engine may further obtain a plurality of confidence metrics associated with the plurality of physiological metrics. Each confidence metric is associated with a corresponding physiological metric and represents a relative likelihood that the physiological metric accurately represents the underlying physiological parameter being measured. Accordingly, each electronic device that generates a physiological metric may also generate a corresponding confidence metric for the same measurement period.

In some variations, a confidence metric may include or be derived from physiological sensor data used to generate a corresponding physiological metric. For example, a confidence metric may include or be derived from a measure of signal strength or another measure of signal quality. Additionally or alternatively, a confidence metric may include or be derived from additional sensor data, such as motion information associated with an electronic device that is used to generate the corresponding physiological metric. In some instances, each electronic device is configured to generate a confidence metric that includes a confidence value (e.g., expressed as a percentage) that may be derived from some or all of the sensors included in that electronic device.

For example, a first electronic device may generate, for a measurement period, a first physiological metric that includes a first heart rate value (e.g., 85 beats per minute) and a first confidence metric that includes a first confidence value (e.g., 95% confidence) corresponding to the first physiological metric. A second electronic device may generate, for the same measurement period, a second physiological metric that includes a second heart rate value (e.g., 95 beats per minute) and a second confidence metric that includes a second confidence value (e.g., 62% confidence) corresponding to the second physiological metric. A decision engine may receive the first and second physiological metrics and the first and second confidence metrics, and the decision engine may use this information in generating an output physiological value for the measurement period. In this example, because the first physiological metric is associated with a higher confidence than the second physiological metric, the decision engine may weigh the first physiological metric more heavily in generating the output physiological value. For example, the decision engine may select the first heart rate value and output the first heart rate value as the output physiological value. In other instances, the decision engine may calculate a heart rate value using the first and second heart rate values and output the calculated heart rate value as the output heart rate value. As a result of weighting the first heart rate value more heavily than the second heart rate value, the calculated heart rate may be closer to the first heart rate than the second heart rate.

Each electronic device that generates a physiological metric for a given physiological parameter includes at least one physiological sensor that is capable of measuring the physiological parameter. For example, in variations where the physiological parameter is heart rate, some or all of the electronic devices may include a heart rate sensor that is configured to measure heart rate. For example, a heart rate sensor may include an optical sensor (e.g., a photoplethysmography (PPG) sensor) or an electrical sensor (e.g., an electrocardiogram (ECG) sensor). It should be appreciated that an electronic device may have multiple different physiological sensors that are configured to measure the same physiological parameter. For example, an electronic device may include two heart rate sensors (e.g., a PPG sensor and an ECG sensor), and either or both heart rate sensors may be used to generate a heart rate metric during a given measurement period. In one example, sensor data from a first heart rate sensor of a given electronic device may be used to generate a physiological metric during one measurement period and sensor data from a second heart rate sensor may be used to generate a physiological metric during another measurement period.

Different electronic devices within a system may include the same or different physiological sensors for measuring a given physiological parameter. In some variations, two electronic devices may include different types of physiological sensors used to measure the same physiological parameter. For example, a first electronic device may include a first type of heart rate sensor (e.g., an optical sensor such as a PPG sensor) and a second electronic device may include a second type of heart rate sensor (e.g., an electrical sensor such as an ECG sensor). Additionally or alternatively, two electronic devices may have the same type of physiological sensors, but with different configurations. For example, a first electronic device may include a heart rate sensor that includes a first optical sensor, and a second electronic device may include a heart rate sensor that includes a second optical sensor. The first and second heart rate sensors may have the same configuration or may have different configurations. Accordingly, the techniques described herein may accommodate measurements performed by a wide variety of physiological sensors for a given physiological parameter.

To allow a decision engine to obtain physiological metrics and confidence metrics from multiple electronic devices, multiple electronic devices may be communicatively connected to each other, such that the multiple electronic devices can transmit information between each other. For example, each electronic device of a system may include a corresponding wireless communication device, such as described in more detail herein, to allow the electronic device to wirelessly communicate with wireless communication devices of other electronic devices of the system. Accordingly, a range of devices may be used to generate the physiological metrics that are used by a decision engine to generate an output physiological value.

In one example, a system may include a pair of ear-worn devices (e.g., a pair of headphones). In these instances, each ear-worn device of the pair may be individually capable of measuring a physiological parameter (e.g., using a corresponding physiological sensor), and thus the pair of ear-worn devices may be considered to be two electronic devices. For a given measurement period, a first ear-worn device may generate a first physiological metric for a given physiological parameter and a second ear-worn device may generate a second physiological metric for the physiological parameter. In some instances, although the pair of ear-worn devices may generate multiple physiological metrics for a given measurement period, the decision engine may only receive a single physiological metric from the pair of ear-worn devices.

Specifically, the pair of ear-worn devices may be operated as a pair of coordinated devices. As used herein, the term "coordinated devices" is used to refer to a set of electronic devices that may operate as a single unit for the purpose of interacting with other electronic devices. For example, a pair of ear-worn devices may be communicably coupled (e.g., paired) with an additional electronic device (e.g., a phone or smartwatch) as a unit. In these instances, the pair of ear-worn devices may communicate with the additional electronic device as if the pair of ear-worn devices was a single device. For example, certain information may be transmitted between the additional electronic device and one or both of the ear-worn devices, whereas other information may be transmitted only between the ear-worn devices (e.g., and not transmitted to the additional electronic device). Specifically, the pair of ear-worn devices may communicate with each other to coordinate operation of the ear-worn devices.

In some instances, a system may include a pair of coordinated devices (e.g., a pair of ear-worn devices) and an additional device (e.g., a smart watch), each of which is configured to generate a corresponding physiological metric for a given measurement period. In these instances the system may include three devices (e.g., a first coordinated device of the pair, a second coordinated device of the pair, and the additional device) that are each capable of independently measuring a given physiological parameter. In some variations, for a given measurement period, a decision engine may obtain three physiological metrics: one from each of the pair of coordinated devices, and one from the additional electronic device. In other variations, the decision engine may obtain only a single physiological metric from the pair of coordinated devices for a measurement period. In these instances, the pair of coordinated devices may cooperate to select a single physiological metric, and the decision engine obtains the selected physiological metric from the pair of coordinated devices and an additional physiological metric from the additional device.

The decision engine may be incorporated into any of these electronic devices or may be incorporated in a separate electronic device that is not configured to measure the physiological parameter. In one example, a smartphone may include a decision engine as described herein and may be communicatively connected to a group of additional electronic devices, such as a smart watch and a pair of ear-worn devices, such that the smartphone may receive physiological metrics from each of these additional electronic devices for a given physiological parameter. The smartphone, depending on its configuration, may or may not be configured to measure the physiological parameter.

When an output physiological value is generated by an electronic device (e.g., using a decision engine incorporated into the electronic device), the output physiological value may be outputted to the user and/or saved for later access by the user. The electronic device used to generate the output physiological value may transmit the output physiological value to other electronic devices within the system. Although a first electronic device (e.g., a smartphone) may generate the output physiological value, a second electronic device (e.g., a smartwatch) may output the output physiological value to the user. In this way, a user may be presented with the output physiological value regardless of which device the user chooses to provide the information. When the output physiological value is outputted the user, it may be presented to the user in any suitable manner. For example, the output physiological value may be displayed via a display (e.g., a display of an electronic device of the system), may be outputted as an audio output via a speaker (e.g., a speaker of an electronic device of the system), or the like.

These and other embodiments are discussed below with reference to FIGS. 1-4. However, those skilled in the art will readily appreciate that the detailed description given herein with respect to these figures is for explanatory purposes only and should not be construed as limiting. The examples described herein are discussed primarily in the context of a sensing system including multiple wearable electronic devices, specifically multiple ear-worn devices and a smartwatch. However, it should be appreciated the concepts described herein may be applied to systems having other combinations of electronic devices that are capable of measuring a particular physiological parameter.

FIG. 1 shows a system 100 that may be used to generate an output physiological value of a physiological parameter. Specifically, the system 100 includes a plurality of devices that includes at least a first electronic device 104 that is configured to receive physiological metrics from multiple additional electronic devices. The first electronic device 104 may include a decision engine 114, which may be configured to obtain a set of physiological metrics and use these physiological metrics to generate a physiological value for a measurement period, as described herein. For example, the decision engine 114 can be configured to use multiple heart rate metrics from different devices to generate an output heart rate value. Example methods by which the decision engine is operated to generate a physiological value is further described herein including in reference to FIGS. 3-4.

The first electronic device 104 may be configured as a wearable electronic device, such as any of the wearable electronic devices described herein, but need not be configured as wearable. In other cases, the first electronic device 104 can be a smartphone, a tablet, a computer (e.g., a laptop or desktop computer), or the like. In some variations, the electronic device includes one or more physiological sensors 112 that are each capable of measuring the physiological parameter. In these instances, at least one of the one or more physiological sensors 112 may be operated to generate a physiological metric for a measurement period, and the decision engine 114 may use this physiological metric as well as those received from other electronic devices in generating an output physiological value for that measurement period.

In the variation shown in FIG. 1, the additional electronic devices include a set of coordinated devices 102, each of which is capable of measuring the physiological parameter. For example, the set of coordinated devices 102 may include a pair of wearable electronic devices, specifically a first wearable electronic device 108*a* and a second wearable electronic device 108*b*. The first wearable electronic device 108*a* and the second wearable electronic device 108*b* may be worn at different locations on a user. For example, the first wearable electronic device 108*a* may be a first ear-worn device that attaches to a first ear of the user (e.g., the right ear) and the second wearable electronic device 108*b* may be a second ear-worn device that attaches to a second ear of the user (e.g., the left ear). In other instances, one or both of the first wearable electronic device 108*a* and the second wearable electronic device 108*b* may be coupled to other locations on a user's body, such as, but not limited to a user's head, torso, arms, legs, hands, or fingers. For example, the first wearable electronic device 108*a* and/or the second wearable electronic device 108*b* may be configured as a head-mounted or head-worn device, a chest strap, a band or bracelet, a ring, or the like.

The individual devices of the set of coordinated devices 102 may be communicatively connected to each other (e.g., using a first communication connection) to coordinate the operation of the individual devices. The set of coordinated devices 102 may be communicatively connected to the first electronic device 104 (e.g., using a second communication connection), such that the set of coordinated devices 102 may transmit physiological metrics to the first electronic device 104. The first and second communication connections may each be any suitable connection that is capable of transmitting information between electronic devices, such as wireless communications protocols including Wi-Fi, Bluetooth, near-field communications (NFC), and/or combinations thereof. The set of coordinated devices 102 may use the first communication connection to determine which physiological metrics will be sent to the first electronic device 104 via the second communication connection.

Each of the set of coordinated devices 102 includes one or more physiological sensors that are capable of measuring the physiological parameter. For example, the first wearable electronic device 108*a* may include a first set of physiological sensors 110*a* and the second wearable electronic device 108*b* may include a second set of physiological sensors 110*b*. The first wearable electronic device 108*a* may operate the first set of physiological sensors 110*a* to generate physiological metrics from a first location of the user's body, and the second wearable electronic device 108*b* may operate the second set of physiological sensors 110*b* to generate physiological metrics from a second location of the user's body.

In some variations, the set of coordinated devices 102 may generate multiple physiological metrics (e.g., from both the first wearable electronic device 108*a* and the second wearable electronic device 108*b*) during a given measurement period, but may only transmit one of these physiological metrics to the first electronic device 104 for the purpose of generating an output physiological value. In these instances, the set of coordinated devices 102 may select one of multiple physiological metrics for transmission to the first electronic device 104. For example, the first wearable electronic device 108*a* may generate a first physiological metric (e.g., a first heart rate metric) for a measurement period and may generate a first confidence metric associated with the first physiological metric. The second wearable electronic device 108*b* may similarly generate a second physiological metric (e.g., a second heart rate metric) for the measurement period and may generate a second confidence metric associated with the second physiological metric. The second wearable electronic device 108*b* may transmit the second measured physiological metric and the second confidence metric to the first wearable electronic device 108*a*, and the first wearable electronic device 108*a* may determine which physiological metric, if any, is transmitted to the first electronic device 104. For example, the first wearable electronic device 108*a* may compare the first and second confidence metrics to select between the first physiological metric and the second physiological metric, and the first wearable electronic device 108*a* may transmit the selected physiological metric (along with the associated confidence metric) to the first electronic device 104. In other instances, the set of coordinated devices 102 may transmit multiple physiological metrics for a measurement period (e.g., the first physiological metric and the second physiological metric).

Additionally or alternatively, some of the coordinated devices 102 may not generate a physiological metric during certain measurement periods. For example, both the first wearable electronic device 108*a* and the second wearable electronic device 108*b* may generate corresponding physiological metrics during a first measurement period. Depending on the confidence metrics associated with these physiological metrics, one of the wearable electronic devices (e.g., the first wearable electronic device 108*a*) may not measure the physiological parameter in one or more subsequent measurement periods and thus will not generate physiological metrics during these subsequent measurement periods. At least one of the wearable electronic devices (e.g., the second wearable electronic device 108*b*) may continue to measure the physiological parameter during these subsequent measurement periods and thereby generate a corresponding physiological metric for each measurement period. Accordingly, the set of coordinated devices 102 will still be able to transmit a physiological metric to the first electronic device 104 for each measurement period, even if only a subset of the devices are measuring the physiological parameter during any given measurement period.

In some cases, the system 100 can include one or more electronic devices 106, either in addition to or instead of the set of coordinated devices 102, each of which is capable of measuring the physiological parameter. Specifically, the electronic device(s) 106 each include one or more physiological sensors 118 that are configured to measure the physiological parameter. Accordingly, the electronic device(s) 106 may each generate a corresponding physiological metric for a given measurement period and may transmit the physiological metric to the first electronic device 104 (e.g., via a corresponding communication connection). Each of the electronic device(s) 106 may have any suitable form factor as may be desired. For example, an electronic device of the electronic device(s) 106 may be configured as a wearable electronic device, a portable electronic device such as a smartphone or a tablet, may be part of or otherwise used with furniture or other support surfaces (e.g., in-bed devices, car seats, or the like), devices such as scales or body composition scanners, or the like.

The electronic devices of the system 100 may include any suitable combination of electronic devices as may be desired. For example, in some variations, the first electronic device 104 may be configured as a smartwatch, and the set of coordinated devices 102 may include a pair of ear-worn devices, such as a pair of headphones, in which the first wearable electronic device 108*a* is a first ear-worn device and the second wearable electronic device 108*b* is a second ear-worn device. Accordingly, the smartwatch may incorporate the decision engine 114, and may generate an output physiological value for a physiological parameter. In some of these variations, the smartwatch includes one or more physiological sensors 112, such that the decision engine 114 obtains, for a given measurement period, a physiological metric from the one or more physiological sensors 112 of the smartwatch and one or more physiological metrics from the pair of ear-worn devices.

In another variation, the first electronic device 104 may be configured as a smartphone, the set of coordinated devices 102 includes a pair of ear-worn devices, and the system 100 includes another electronic device (e.g., one of the electronic device(s) 106) configured as a smartwatch. In these instances, the smartphone may incorporate the decision engine 114, and may generate an output physiological value using physiological metrics received from the smartwatch and the pair of ear-worn devices. It should also be appreciated that the system 100 may be dynamically reconfigured as electronic devices are added and removed. For example, a user may take off a pair of headphones and start using a different pair of headphones or a head-mounted device. In these instances, the system 100 may be updated to include the new device being worn by the user and may instead use physiological metrics generated by the new device in calculating output physiological values for a physiological parameter.

Figure 2A:
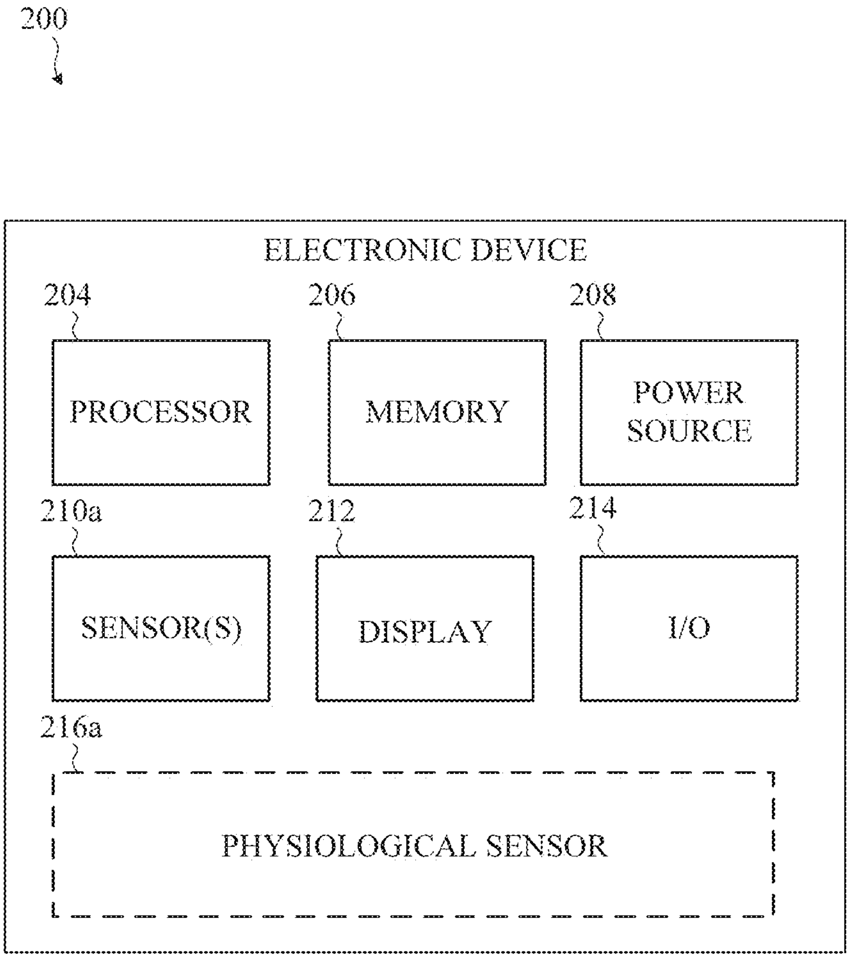
FIGS. 2A and 2B show a block diagram of a system including multiple electronic devices that can be used to determine a physiological parameter of a user.
Figure 2B:
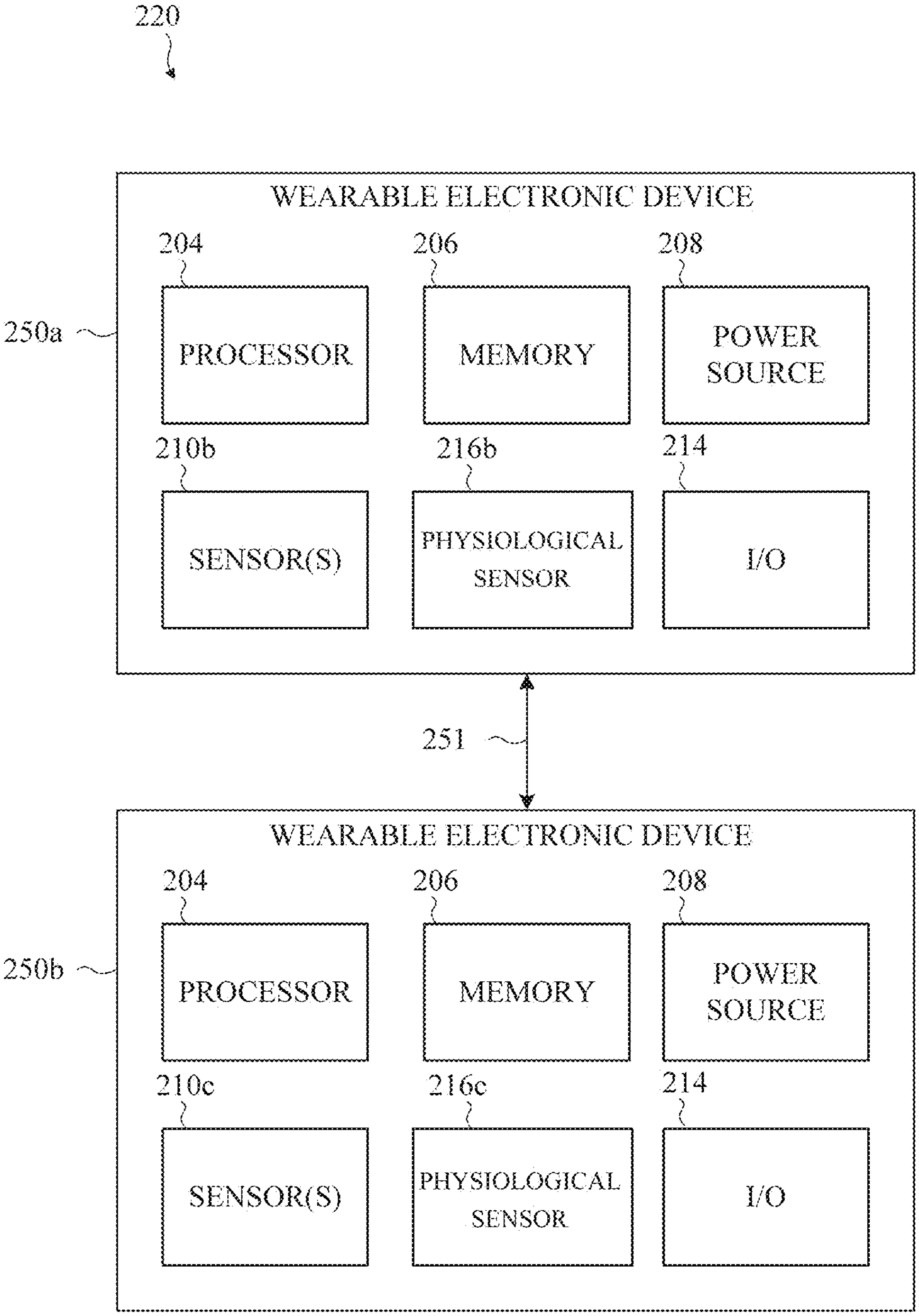

FIGS. 2A and 2B show block diagrams of example components of electronic devices that may be used in the systems described herein. For example, FIG. 2A shows an electronic device 200. Any of the electronic devices of FIG. 1 may be configured to include some or all of the components of electronic device 200. The electronic device 200 can include a processor 204, memory 206, a power source 208, one or more sensors 210*a*, a display 212, and an input/output (I/O) unit 214. In instances where the electronic device 200 is configured to measure a physiological parameter (e.g., such as the electronic device 106 of FIG. 1), the electronic device 200 may also include a physiological sensor 216*a*.

The processor 204 can control some or all of the operations of the electronic device 200. The processor 204 can communicate, either directly or indirectly, with some or all of the components of the electronic device 200. For example, a system bus or other communication mechanism may interconnect the various components of the electronic device 200, including the processor 204, the memory 206, the power source 208, the one or more sensors 210*a*, the display 212, the I/O unit 214, and the physiological sensor 216*a*.

The processor 204 can be implemented as any component capable of processing, receiving, or transmitting data or instructions. For example, the processor 204 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 200 can be controlled by multiple processors. For example, select components of the electronic device 200 (e.g., a one of the sensor(s) 210*a*) may be controlled by a first processor and other components of the electronic device (e.g., the I/O unit 214) may be controlled by a second processor, where the first and second processors may or may not be in communication with each other.

The memory 206 can store electronic data that can be used by the electronic device. For example, the memory 206 can store electrical data or content such as, for example, measured electrical signals, audio and video files, documents and applications, device settings and user preferences, timing signals, control signals, and data structures or databases. The memory 206 can be configured as any type of memory. By way of example only, the memory 206 can be implemented as random access memory, read-only memory, Flash memory, removable memory, other types of memory storage elements, or combinations of such devices. In instances where the electronic device 200 includes a decision engine, the memory 206 may store instructions that, when executed by the processor 204, cause the processor 204 to perform the various operations of the decision engine. In instances where the electronic device 200 includes a physiological sensor 216*a*, the memory 206 may store instructions that, when executed by the processor 204, cause the processor 204 to generate a physiological metric and a confidence metric as described herein.

The power source 208 can be implemented with any device capable of providing energy to the electronic device 200. For example, the power source 208 may be one or more batteries or rechargeable batteries. Additionally or alternatively, the electronic device 200 may be configured to be powered by mains power, and the power source 208 may include any power control circuitry as may be needed to utilize the mains power.

The electronic device 200 may also include one or more sensors 210*a*, in addition to or instead of the physiological sensor 216*a*. The sensor(s) 210*a* may be configured to measure one or more additional parameters associated with the electronic device 200, a user engaging with the electronic device 200, and/or the environment around the device 200. For example, the sensor(s) 210*a* may be configured to measure temperature (e.g., using a temperature sensor), device motion and/or orientation (e.g., using a motion sensor such as an accelerometer, gyroscope, or the like), sound (e.g., using a microphone), or the like. In some variations, the sensor(s) 210*a* may include one or more additional physiological sensors that are configured to measure one or more additional physiological parameters. For example, in instances where the electronic device 200 is used as part of a system (e.g., system 100) to generate an output heart rate value, the electronic device 200 may include physiological sensors configured to measure other physiological parameters such as respiration rate, blood oxygen saturation, or the like. It should also be appreciated that a single physiological sensor (e.g., the physiological sensor 216*a*) may be capable of measuring multiple physiological parameters. For example, certain configurations of an optical sensor may be capable of measuring heart rate, heart rate variability, and blood oxygen saturation.

In some instances, information from the sensor(s) 210*a* may be used in generating an output physiological value of a physiological parameter. For example, in variations in which the sensor(s) 210*a* include a motion sensor, the motion sensor may generate a motion signal. In some instances, the motion signal may be used in determining a current activity being performed by a user. For example, in instances where the device is configured as a smartwatch, a motion signal generated by the smartwatch may be used to identify whether a user is stationary, walking, running, or engaging in one or more other activities. Additionally or alternatively, a motion signal generated during a measurement period may be used in generating a physiological metric or a confidence metric associated with the measurement period. For example, in variations where sensor data from the physiological sensor 216*a* is used to generate a physiological metric (e.g., a heart rate value as part of a heart rate metric), the motion signal may be used to generate the physiological metric. Specifically, the motion signal may help reduce the impact of motion artifacts that may present in sensor data generated by the physiological sensor 216*a*. Similarly, when a confidence metric is generated for an associated physiological metric, the motion signal may be used in generating the confidence metric. The amount or nature of the motion measured by the motion signal may be indicative of the accuracy of the physiological metric. For example, measurements associated with lower motion levels may be more likely to be accurate as compared to measurements taken at higher motion levels.

The I/O unit 214 can include components that facilitate the transmission and collection of information by the electronic device 200. For example, in instances where the electronic device 200 is configured to wirelessly communicate with another electronic device (e.g., to communicatively connect the electronic devices), the I/O unit 214 includes a wireless communication device that can wirelessly transmit and/or receive data from a user or another electronic device. A wireless communication device may use any suitable communication protocol, such as NFC, radiofrequency (RF), cellular, Wi-Fi, Bluetooth, infrared (IR) communication, or the like. In some variations, the I/O unit 214 may be configured to transmit and/or receive data via a wired network connection, such as an Ethernet connection. The I/O unit 214 may include one or more input devices, such as buttons, dials, or the like, that may allow the electronic device 200 to receive user inputs.

The electronic device 200 may also include a display 212. The display 212 may include a display which may be implemented as a liquid-crystal display (LCD), organic light-emitting diode (OLED) display, light-emitting diode (LED) display, or the like. If the display is an LCD, the display may also include a backlight component that can be controlled to provide variable levels of display brightness. If the display is an OLED or LED type display, the brightness of the display 212 may be controlled by modifying the electrical signals that are provided to display elements. In some instances, the display 212 may be used to output a unified physiological value to a user.

In variations where the systems described here include a set of coordinated devices, the coordinated devices may have the same or different configuration. For example, FIG. 2B shows a set of coordinated devices 220 such as described herein. The set of coordinated devices 220 is shown as having a first wearable electronic device 250*a* and a second wearable electronic device 250*b*. The first wearable electronic device 108*a* and the second wearable electronic device 108*b* of the set of coordinated devices 102 of FIG. 1 may include any of the components of the first wearable electronic device 250*a* and the second wearable electronic device 250*b*.

Each of the first wearable electronic device 250*a* and the second wearable electronic device 250*b* may include a corresponding processor 204, memory 206, power source 208, and I/O unit 214, such as described herein with respect to the electronic device 200 of FIG. 2A. The I/O units of the first wearable electronic device 250*a* and the second wearable electronic device 250*b* may allow the devices to establish a communication channel 251 (e.g., using corresponding wireless communication devices) to allow the first wearable electronic device 250*a* and the second wearable electronic device 250*b* to coordinate their operation. Additionally, the first wearable electronic device 250*a* may include a physiological sensor 216*b* and the second wearable electronic device 250*b* may include a physiological sensor 216*c*, each of which is configured to measure a physiological parameter. The first wearable electronic device 250*a* may generate a first physiological metric during a measurement period using the physiological sensor 216*b*, and the second wearable electronic device 250*b* may generate a second physiological metric during the measurement period using the physiological sensor 216*c*.

The physiological sensors 216*b*, 216*c* may have the same configuration or different configurations. For example, in some variations the physiological sensor 216*b* of the first wearable electronic device 250*a* may be a first type of sensor (e.g., an electrical sensor such as an ECG sensor) and the physiological sensor 216*c* of the second wearable electronic device 250*b* may be a second type of sensor (e.g., an electrical sensor such as an optical sensor). In other variations, the physiological sensors 216*b*, 216*c* may both be the same type of sensor, such as an optical sensor. In instances where the set of coordinated devices 220 is used in the same system as the electronic device 200 of FIG. 2A, the physiological sensors 216*b*, 216*c* may each have the same or different configuration as the physiological sensor 216*a* of the electronic device 200.

The first wearable electronic device 250*a* may include one or more sensors 210*b* in addition to the physiological sensor 216*b*. Similarly, the second wearable electronic device 250*b* may include one or more sensors 210*c* in addition to the physiological sensor 216*b*. The sensor(s) 210*b* of the first wearable electronic device 250*a* may be the same as or different than the sensor(s) 210*c* of the second wearable electronic device 250*b*. In instances where the set of coordinated devices 220 is used in the same system as the electronic device 200 of FIG. 2A, the sensors 210*b*, 210*c* of the set of coordinated devices 220 may be the same as or different from the sensor(s) 210*a* of the electronic device 200. In some variations, each of the first wearable electronic device 250*a* and the second wearable electronic device 250*b* may include a motion sensor that generates a corresponding motion signal.

In some variations, the first wearable electronic device 250*a* and the second wearable electronic device 250*b* do not include a display. In these variations, the set of coordinated devices 220 may output information to a user via another electronic device (e.g., via the display 212 of the electronic device 200 of FIG. 2A). Additionally or alternatively, one or both of the first and second wearable electronic devices 250*a*, 250*b* may include a corresponding speaker, and may output information to a user via an audio output. For example, when a decision engine generates an output physiological value for a given measurement period (e.g., using one or more physiological metrics generated by the set of coordinated devices 220), the generated output physiological value may be outputted to the user as an audio prompt via one or more speakers of the set of coordinated devices 220. In some variations, one or both of the first and second wearable electronic devices 250*a*, 250*b* may include a corresponding display (not shown), which may be used to output information to the user.

Figure 3:
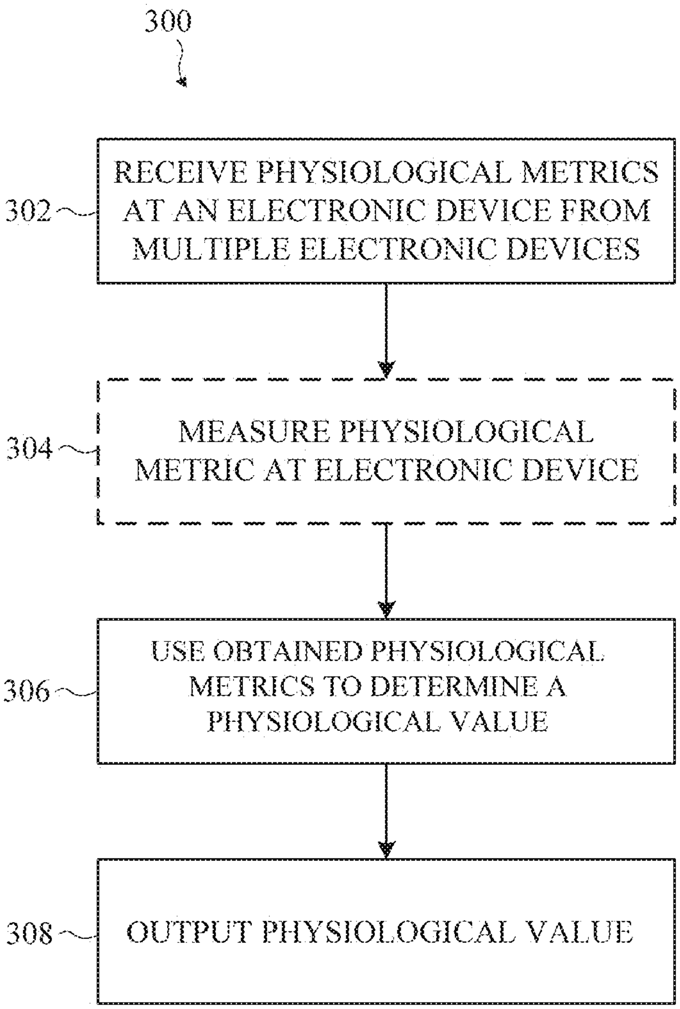
FIG. 3 shows an example method for operating a system of multiple electronic devices to determine a physiological parameter of a user.

FIG. 3 shows an example method 300 for operating a system of multiple electronic devices to determine physiological parameters of a user. The method 300 can be performed by the systems and devices described herein.

At operation 302, the method 300 can include receiving, at an electronic device that includes a decision engine, physiological metrics from multiple other electronic devices. For example, in some variations, a system may include an electronic device that includes a decision engine as described herein, and may further include a first wearable electronic device, a second wearable electronic device, and a third wearable electronic device, each of which includes a corresponding physiological sensor configured to measure a physiological parameter. In this way, each of the first wearable electronic device, the second wearable electronic device, and the third wearable electronic device is capable of generating a corresponding physiological metric. Specifically, the first wearable electronic device is configured to generate a first physiological metric, the second wearable electronic device is configured to generate a second physiological metric, and the third wearable electronic device is configured to generate a third physiological metric.

In some of these variations, the physiological parameter is heart rate and each of the first wearable electronic device, the second wearable electronic device, and the third wearable electronic device include a corresponding heart rate sensor that is configured to measure heart rate. Accordingly, the first wearable electronic device, the second wearable electronic device, and the third wearable electronic device are capable of generating, respectively, a first heart rate metric, a second heart rate metric, and a third heart rate metric. In some variations, the corresponding heart rate sensor of each of the first wearable electronic device, the second wearable electronic device, and the third wearable electronic device is an optical sensor.

The electronic device may, for any given measurement window, receive some or all of the first physiological metric (e.g., the first heart rate metric), the second physiological metric (e.g., the second heart rate metric), and the third physiological metric (e.g., the third heart rate metric). For example, each electronic device of the system may include a corresponding wireless communication device, such as described in more detail herein, which allows that electronic device to receive and/or transmit information with another electronic device (e.g., via its wireless communication device). In some variations, each of the first wearable electronic device, the second wearable electronic device, and the third wearable electronic device are configured to directly transmit its corresponding physiological metric to the electronic device. In other variations, two or more of the wearable electronic devices may coordinate which physiological metrics are transmitted to the electronic device.

For example, in some variations, the first wearable electronic device and the second wearable electronic device may be part of a set of coordinated devices as described herein. For example, in some variations the first wearable electronic device may be a first ear-worn device located at a first ear (e.g., the right ear) and the second wearable electronic device may be a second ear-worn device located at a second ear (e.g., the left ear). In some of these variations, the first wearable electronic device includes a first wireless communication device and the second wearable electronic device includes a second wireless communication device. The first wearable electronic device is configured to operate a first physiological sensor to generate the first physiological metric from a first location on a user. Similarly, the second wearable electronic device is configured to operate a second physiological sensor to generate the second physiological metric from a second location on the user.

The second wearable electronic device may operate the second wireless communication device to transmit the second physiological metric to the first wearable electronic device. The first wearable electronic device is configured to compare the first physiological metric to the second physiological metric for a first measurement window. The first wearable electronic device is further configured to operate the first wireless communication device to transmit, for the first measurement window, one of the first physiological metric or the second physiological metric to the electronic device based on this comparison. In this way, the electronic device may receive one of the first physiological metric or the second physiological metric for a given window.

In some variations, comparing the first physiological metric to the second physiological metric may include comparing confidence values associated with the first physiological metric and the second physiological metric. Specifically, the first wearable electronic device and the second wearable electronic device may be configured to generate corresponding confidence metrics, such as described in more detail herein, associated with the respective physiological metrics (e.g., the first wearable electronic device generates a first confidence metric associated with the first physiological metric and the second wearable electronic device generates a second confidence metric associated with the second physiological metric). In these instances, the second wearable electronic device may transmit the second confidence metric to the first wearable electronic device along with the second physiological metric. In comparing the first physiological metric and the second physiological metric for a given measurement period, the first wearable electronic device may compare the first confidence metric and the second confidence metric to determine which physiological metric to select. Accordingly, the first wearable electronic device can select one of the first physiological metric or the second physiological metric to send to the electronic device based on the comparison. For example, the first wearable electronic device can be configured to select the physiological metric having a greater confidence metric (e.g., the confidence metric that indicates a higher likelihood of accuracy).

This selection may occur at different points in time, and thus the first wearable electronic device may transmit the first physiological metric for certain measurement windows and may transmit the second physiological metric for other measurement windows. For example, for a first measurement window, the first wearable electronic device may make a first comparison of confidence metrics for the first and second physiological metrics. The first wearable electronic device may select one of the first physiological metric or the second physiological metric based on this first comparison and may transmit the selected physiological metric to the electronic device. In this way, the electronic device may use the selected first physiological metric or the second physiological metric, as well as the third physiological metric received from the third wearable electronic device, to generate a first output physiological value (e.g., a first heart rate value) for the first measurement window.

For a second measurement window, the first wearable electronic device may make a second comparison of confidence metrics for the first and second physiological metrics. The first wearable electronic device may select one of the first physiological metric or the second physiological metric based on this second comparison and may transmit the selected physiological metric to the electronic device. In this way, the electronic device may use the selected first physiological metric or the second physiological metric, as well as the third physiological metric received from the third wearable electronic device, to generate a second output physiological value (e.g., a second heart rate value) for the second measurement window.

It should be appreciated that a comparison between the confidence metrics associated with the first and second physiological metrics need not be made for every measurement period. For example, the first comparison of the confidence metrics of the first and second physiological metrics may precede the first measurement window. In this way, the first comparison may use values of the confidence metrics that are associated with an additional measurement window that precedes the first measurement window. In this way, the selection of the first physiological metric or the second physiological metric may remain in place until a certain condition is met (e.g., until the confidence metric associated with the selected physiological metric falls below a threshold level). Additionally or alternatively, the second comparison of the confidence metrics of the first and second physiological metrics may precede the second measurement window.

In instances where the selection of the first physiological metric or the second physiological metric is performed before the start of a measurement window, the physiological sensor associated with the non-selected physiological metric may be deactivated for at least a portion of that measurement window. In the example where the second comparison of the confidence metrics precedes the second measurement window, the first wearable electronic device may select between the first physiological metric and the second physiological metric before the start of the measurement window. If the first physiological metric is selected for the second measurement window, the second physiological sensor may be deactivated for at least a portion of the measurement window. Similarly, if the second physiological metric is selected for the second measurement window, the first physiological sensor may be deactivated for at least a portion of the measurement window. Accordingly, only one of the first and second wearable electronic devices may be used to measure the physiological parameter during these times.

The deactivated sensor may remain deactivated until a certain condition is met. In some instances, the deactivated sensor (e.g., the second physiological sensor) may remain deactivated until the confidence metric associated with the physiological parameter of the active sensor (e.g., the first confidence metric for the first physiological metric generated by the first physiological sensor) falls below a threshold level. In these instances, so long as the active sensor is producing physiological metrics with a sufficient level of confidence, the respective physiological metric may continue to be selected for transmission to the electronic device. Additionally or alternatively, the deactivated sensor may be re-activated after a threshold amount of time, at which point an additional comparison of the first and second confidence metrics may be performed, and a new selection between the first physiological metric and the second physiological metric may be performed.

Similarly, the third wearable electronic device may be configured to generate a third confidence metric associated with the third physiological metric. In some instances, the third wearable electronic device may be configured to deactivate the third physiological sensor for one or more measurement periods. In some of these variations, if the third confidence metric is below a first threshold and/or the first or second confidence metric is above a second threshold, the third wearable electronic device may deactivate the third physiological sensor for at least a portion of a subsequent measurement period. For example, if the third confidence metric falls below a defined threshold during the second measurement period, the third wearable electronic device may deactivate the third physiological sensor for at least a portion of a third measurement period subsequent to the second measurement period. During this third measurement period, the electronic device may generate a third output physiological value using whichever of the first heart rate metric or the second heart rate metric is selected, by the first wearable electronic device, for the third measurement period.

At operation 304, the method 300 can include measuring the physiological parameter at the electronic device to generate a corresponding physiological metric. That is, in some cases, the electronic device can include one or more physiological sensors (e.g., a fourth physiological sensor) and operate the physiological sensors to generate a physiological metric (e.g., a fourth physiological metric), as described herein. For example, in variations where the physiological parameter is heart rate, the electronic device may include a fourth heart rate sensor that may be used to generate fourth heart rate metrics.

Additionally, the electronic device can be configured to generate a corresponding confidence metric for the fourth physiological metric (e.g., a fourth confidence metric), which may be used in generating an output physiological value. Accordingly, the decision engine of the electronic device may obtain, for a given measurement window, one or more physiological metrics from the first, second, and third wearable electronic devices (e.g., one or more of the first physiological metric, the second physiological metric, and the third physiological metric), as well as the fourth physiological metric measured at the electronic device.

At operation 306, the method 300 can include the electronic device using the obtained physiological metrics to determine a physiological value for each measurement window. For example, at operation 306, the method 300 may generate a first output physiological value for the first measurement period. The first output physiological value represents the electronic device's selection, based on the physiological metrics obtained by the decision engine, of a representative value of the physiological parameter being measured by the system. For example, when the physiological parameter is heart rate, the first output physiological value may include a first heart rate value. Similarly, the decision engine may generate corresponding output physiological values for different measurement windows (e.g., a second output physiological value for a second measurement window, a third output physiological value for a third measurement window, and so on).

In some variations, the output physiological value generated for a given measurement period may be generated using the confidence metrics for the obtained physiological metrics. For example, when the first wearable electronic device transmits a selected physiological metric to the electronic device, the first wearable electronic device may also transmit the corresponding confidence value (e.g., the first wearable electronic device may transmit the first physiological metric and the first confidence metric or may transmit the second physiological metric and the second confidence metric). Similarly, the third wearable electronic device may be configured to transmit the third confidence metric to the electronic device with the third physiological metric. Accordingly, the decision engine may obtain, for a given measurement period, confidence metrics (e.g., some or all of the first, second, third, and fourth confidence metrics) for the physiological metrics that are obtained for the measurement period.

The decision engine may utilize the confidence metrics in any suitable manner. For example, in some variations, one of the obtained physiological metrics will be selected based on a comparison of the obtained confidence metrics. In some of these variations, one of the obtained physiological metrics with the greatest associated confidence metric is selected, and the selected physiological metric is used to generate the output physiological value. In other variations, the output physiological value may be generated using a weighted combination of the obtained physiological metrics, wherein the relative contribution of the different physiological metrics is based at least on the obtained confidence metrics (e.g., physiological metrics with higher confidence may be weighed more heavily).

It should be appreciated that the obtained confidence metrics may be one of multiple factors used in generating the output physiological value for a measurement period. For example, in some variations, the decision engine may determine an activity associated with a given measurement period, and may use the determined activity in generating the output physiological value for that measurement period. Certain activities may have different relative impacts on the physiological metrics generated by the various devices of the system. For example, it may be possible for a first type of activity to have a larger impact on measurements performed by the first and second wearable electronic devices as compared to measurements performed by the third wearable electronic device. In these instances, although the first or second wearable electronic device may generate a physiological metric having a relatively high confidence (e.g., as indicated by a corresponding confidence metric), it may still be desirable to prioritize the physiological metric of the third wearable electronic device.

Accordingly, in some variations the decision engine may generate a set of weight parameters associated with the obtained physiological metrics. Each obtained physiological metric may be associated with a corresponding weight parameter of the set of weight parameters, which represents the relative priority that will be applied to that physiological metric when generating the output physiological values. In some variations, the set of weight parameters may be based on the obtained confidence metrics. For example, the first or the second physiological metric that is selected by the first wearable electronic device and obtained by the decision engine, may be associated with a first weight parameter. The first weight parameter may be generated using at least the confidence metric associated with the selected physiological metric (e.g., the first confidence metric or the third confidence metric). Similarly, the third physiological metric may be associated with a second weight parameter, which may be generated using at least the confidence metric associated with the third physiological metric. In instances where the electronic device generates a fourth physiological metric, the fourth physiological metric may be associated with a third weight parameter, which may be generated using at least the confidence metric associated with the fourth physiological metric.

In some variations, each of the set of weight parameters may be selected using a determined activity. In this way, the determined activity may alter the relative weight given to the obtained physiological metrics, and is thus used by the decision engine in generating the output physiological value. The activity associated with a measurement window may be determined in any suitable manner. In some instances, the activity may be determined from motion information generated by one or more of the electronic devices in the system. For example, some or all of the first wearable electronic device, the second wearable electronic device, and the third wearable electronic device may include a corresponding motion sensor, and thus may generate motion information that may be used to determine the activity. For example, in some variations, the third wearable electronic device may include a motion sensor that generates a motion signal. The motion signal may be analyzed to estimate an activity currently being performed by the user. In another example, one or both of the first and second wearable electronic devices may also include a corresponding motion sensor, and motion information from the first and second wearable electronic devices, as well as motion information from the third wearable electronic device, is used to estimate an activity currently being performed by the user. Sensor information from additional sensors may also be used to help to determine a current activity. Additionally or alternatively, user input may be used to determine a current activity. For example, a user may use a software application on one of the electronic devices to initiate tracking of a workout session, and the user may specify what activity they are engaging in.

While motion information generated by various electronic devices of the system may be used in generating confidence metrics and/or determining a user activity, in some instances it may be desirable for the decision engine to obtain a motion signal associated with a physiological metric. For example, the decision engine may obtain a set of motion signals associated with the obtained physiological metrics. Each motion signal may be captured by a motion sensor of the electronic device used to generate a corresponding physiological metric, and may be transmitted to or otherwise received by the decision engine. The set of motion signals may be used by the decision engine in generating the output physiological values. For example, in some variations, the set of weight parameters may be selected using the set of motion signals. In these instances, physiological metrics associated with lower levels of motion may be weighed more heavily in generating the output physiological value.

It should be appreciated that the set of weight parameters may be reselected with each measurement window, as the information used to generate the set of weight parameters is updated. For example, a first set of weight parameters may be selected for a first measurement window. The first set of weight parameters may depend at least on the confidence metrics associated with the physiological metrics obtained for the first measurement window. In some variations, the first set of weight parameters may also depend at least partially on an activity determined for the first measurement window and/or one or more motion signals associated with the physiological metrics. The decision engine may generate, using the obtained physiological metrics and the first set of weight parameters, a first output physiological value for the first measurement window.

For a second measurement window, a second set of weight parameters may be selected. The second set of weight parameters may depend at least on the confidence metrics associated with the physiological metrics obtained for the second measurement window. In some variations, the second set of weight parameters may also depend at least partially on an activity determined for the second measurement window and/or one or more motion signals associated with the physiological metrics. The decision engine may generate, using the obtained physiological metrics and the second set of weight parameters, a second output physiological value for the second measurement window. Accordingly, the decision engine may continue to generate output physiological values for subsequent measurement windows, and thus may provide a unified output of the physiological value over time.

At operation 308, the method 300 can include outputting the physiological value (e.g., heart rate value) to a user, such as described in more detail herein. Accordingly, the electronic device (or another device in the system, such as the first wearable electronic device, the second wearable electronic device, or the third wearable electronic device) may output the generated output physiological value to the user. In this way, the user will be able to obtain a single value for the measured physiological parameter at each point in time, as opposed to potentially receiving differing values from the individual devices.

Figure 4:
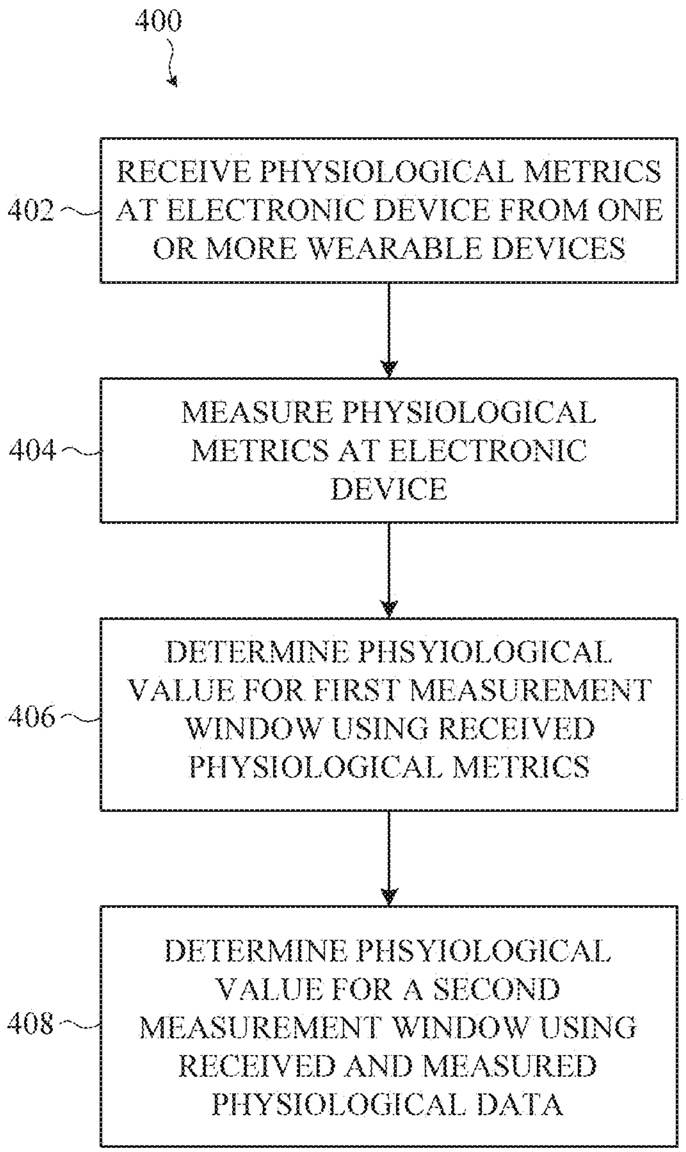
FIG. 4 shows an example method for operating a system of multiple electronic devices to determine a physiological parameter of a user.

While the method 300 of FIG. 3 discusses an electronic device that receives multiple physiological metrics from additional electronic devices, in other instances it may be possible for an electronic device to receive a single physiological metric from other devices for a given measurement window. FIG. 4 shows an example method 400 for operating a system of multiple electronic devices to determine physiological parameters of a user. The method 400 can be performed by the systems and devices described herein. For example, the method 400 can be performed by the system described in relation to method 300, except that the third wearable electronic device may instead include the decision engine. In these instances, the operations of the electronic device and the decision engine may instead be performed by the third wearable electronic device.

At operation 402, the method 400 can include receiving, at an electronic device that includes a decision engine, one or more physiological metric from one or more other electronic devices. For example, using the system described with respect to the method of FIG. 3, the third wearable electronic device may receive a physiological metric (e.g., either the first physiological metric or the second physiological metric) that is selected by the first wearable electronic device and transmitted to the third wearable electronic device for a measurement window. The selection of the physiological metric to transmit to the third wearable electronic device may be performed in any manner as described herein. To the extent that the system includes multiple additional electronic devices, the third wearable electronic device may also receive physiological metrics from these devices for the measurement window.

At operation 404, the method 400 can include measuring a physiological parameter at the electronic device. For example, using the system described with respect to the method of FIG. 3, the third wearable electronic device may generate the third physiological metric as discussed in more detail herein. Additionally, the third wearable electronic device may generate a third confidence metric for the third physiological metric. Overall, the third wearable electronic device may obtain multiple physiological metrics for some measurement windows, wherein the obtained physiological metrics include the selected one of the first physiological metric or the second physiological metric received from the first wearable electronic device, as well as the third physiological metric generated by the third physiological device. During other measurement windows, depending on whether one or more physiological sensors have been deactivated, such as described herein, the obtained physiological metrics include only received physiological metrics or only measured physiological metrics.

For example, at operation 406, the method 400 can include generating an output physiological value for a first measurement window using only physiological metrics that are received from other devices. For example, the third physiological sensor of the third wearable electronic device may be deactivated for at least a portion of the first measurement window, such that the third wearable electronic device is not generating the third physiological metric during this time. Accordingly, the physiological metric(s) received by the third wearable electronic device (e.g., the selected one of the first physiological metric and the second physiological metric) may be used to determine a first output physiological value for the first measurement period.

At operation 408, the method 400 can include determining a second output physiological value for a second measurement window using a combination of received and measured physiological metrics. For example, the third wearable electronic device may obtain a set of physiological metrics that includes the selected one of the first physiological metric or the second physiological metric received from the first wearable electronic device, as well as the third physiological metric generated by the third physiological device. The physiological metrics used to generate the output physiological value may be updated with each measurement window, as the availability and/or quality of different measurements changes.

In some embodiments, a method as described herein (such as method 300 or method 400), is performed at a first computer system (as described herein) via a system process (e.g., an operating system process, a server system process) that is different from one or more applications executing and/or installed on the first computer system.

In some embodiments, the method is performed at a first computer system (as described herein) via a system process (e.g., an operating system process, a server system process) that is different from one or more applications executing and/or installed on the first computer system.

In some embodiments, the method is performed at a first computer system (as described herein) by an application that is different from a system process. In some embodiments, the instructions of the application, when executed, control the first computer system to perform the method by calling an application programming interface (API) provided by the system process. In some embodiments, the application performs at least a portion of the method without calling the API.

In some embodiments, the application can be any suitable type of application, including, for example, one or more of: a browser application, an application that functions as an execution environment for plug-ins, widgets or other applications, a fitness application, a health application, a digital payments application, a media application, a social network application, a messaging application, and/or a maps application.

In some embodiments, the application is an application that is pre-installed on the first computer system at purchase (e.g., a first party application). In other embodiments, the application is an application that is provided to the first computer system via an operating system update file (e.g., a first party application). In other embodiments, the application is an application that is provided via an application store. In some implementations, the application store is pre-installed on the first computer system at purchase (e.g., a first party application store) and allows download of one or more applications. In some embodiments, the application store is a third-party application store (e.g., an application store that is provided by another device, downloaded via a network, and/or read from a storage device). In some embodiments, the application is a third-party application (e.g., an app that is provided by an application store, downloaded via a network, and/or read from a storage device). In some embodiments, the application controls the first computer system to perform the method by calling an application programming interface (API) provided by the system process using one or more parameters.

In some embodiments, at least one API is a software module (e.g., a collection of computer-readable instructions) that provides an interface that allows a different set of instructions (e.g., API calling instructions) to access and use one or more functions, methods, procedures, data structures, classes, and/or other services provided by a set of implementation instructions of the system process. The API can define one or more parameters that are passed between the API calling instructions and the implementation instructions.

In some embodiments, the set of implementation instructions is a system software module (e.g., a collection of computer-readable instructions) that is constructed to perform an operation in response to receiving an API call via the API. In some embodiments, the set of implementation instructions is constructed to provide an API response (via the API) as a result of processing an API call. In some embodiments, the set of implementation instructions is included in the device that runs the application. In some embodiments, the set of implementation instructions is included in an electronic device that is separate from the device that runs the application.

As described above, one aspect of the present technology involves the collection of physiological information of a user. The present disclosure contemplates that in some instances this gathered data may include personal information data that uniquely identifies or can be used to contact or locate a specific person. Such personal information data can include demographic data, location-based data, telephone numbers, email addresses, Twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining the privacy and security of personal information data. Such policies should be easily accessible by users and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and revised to adhere to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A system for determining a heart rate of a user, the system comprising:

a first wearable electronic device comprising a first heart rate sensor and a first wireless communication device, the first wearable electronic device configured to operate the first heart rate sensor to detect a first heart rate metric at a first location on the user;

a second wearable electronic device comprising a second heart rate sensor and a second wireless communication device, the second wearable electronic device configured to:

operate the second heart rate sensor to detect a second heart rate metric at a second location on the user; and operate the second wireless communication device to transmit the second heart rate metric to the first wearable electronic device;

a third wearable electronic device comprising a third heart rate sensor and a third wireless communication device, the third wearable electronic device configured to operate the third heart rate sensor to detect a third heart rate metric at a third location on the user, wherein:

the first wearable electronic device is configured to:

compare the first heart rate metric to the second heart rate metric for a first measurement window; and operate the first wireless communication device to transmit, for the first measurement window, one of the first heart rate metric or the second heart rate metric to the third wearable electronic device based on the comparison; and the third wearable electronic device is configured to:

use the received one of the first heart rate metric or the second heart rate metric, and the third heart rate metric, to generate a heart rate value for the user for the first measurement window; and cause the generated heart rate value to be output to the user.

2. The system of claim 1, wherein:

comparing, by the first wearable electronic device, the first heart rate metric to the second heart rate metric comprises comparing a first confidence metric associated with the first heart rate metric to a second confidence metric associated with the second heart rate metric; and the first wearable electronic device selects the one of the first heart rate metric or the second heart rate metric associated with a greater confidence metric for transmitting to the third wearable electronic device.

3. The system of claim 1, wherein each of the first heart rate sensor, the second heart rate sensor and the third heart rate sensor comprise an optical sensor.

4. The system of claim 1, wherein, in response to the third wearable electronic device selecting the received one of the first heart rate metric or the second heart rate metric to generate the heart rate value, the third wearable electronic device is configured to deactivate the third heart rate sensor.

5. The system of claim 1, wherein, the third wearable electronic device is configured to:

monitor a confidence metric associated with the received one of the first heart rate metric or the second heart rate metric;

in response to the confidence metric falling below a confidence threshold:

cause the first wearable electronic device to compare, for a second measurement window, the first heart rate metric to the second heart rate metric; and transmit one of the first heart rate metric or the second heart rate metric for the second measurement window to the third wearable electronic device based on the comparison for the second measurement window.

6. The system of claim 1, wherein the first wearable electronic device is configured to:

compare the first heart rate metric to the second heart rate metric at a defined interval; and for each comparison at the defined interval, select the one of the first heart rate metric or the second heart rate metric to transmit to the third wearable electronic device.

7. The system of claim 1, wherein:

the third wearable electronic device comprises a motion sensor configured to detect motion and generate a motion signal; and the third wearable electronic device is configured to select the received one of the first heart rate metric or the second heart rate metric or the third heart rate metric to generate the heart rate value based on the motion signal.

8. The system of claim 7, wherein:

the third wearable electronic device is configured to determine an activity of the user using the motion signal; and select the received one of the first heart rate metric or the second heart rate metric, or the third heart rate metric to generate the heart rate value based on the determined activity.

9. The system of claim 1, wherein the third wearable electronic device is configured to generate the heart rate value by:

applying a weight parameter to the third heart rate metric, the weight parameter determined using a corresponding confidence metric.

10. The system of claim 1, wherein the third wearable electronic device is configured to generate the heart rate value by:

applying a first weight parameter to the received one of the first heart rate metric and the second heart rate metric, the first weight parameter determined using a first confidence metric determined for the received one of the first heart rate metric and the second heart rate metric; and applying a second weight parameter to the third heart rate metric, the second weight parameter determined using a second confidence metric determined for the third heart rate metric.

11. A system for determining a heart rate of a user, the system comprising:

a first wearable electronic device comprising a first heart rate sensor and a first wireless communication device, the first wearable electronic device configured to operate the first heart rate sensor to determine a first heart rate metric at a first location on the user;

a second wearable electronic device comprising a second heart rate sensor and a second wireless communication device, the second wearable electronic device configured to operate the second heart rate sensor to determine a second heart rate metric at a second location on the user; and a third wearable electronic device comprising a third heart rate sensor and a third wireless communication device, the third wearable electronic device configured to:

operate the third heart rate sensor to determine a third heart rate metric at a third location on the user;

receive at least one of the first heart rate metric and the second heart rate metric;

determine, for a first measurement window, a first heart rate value for the user using the received one of the first and second heart rate metrics, the third hear rate metric, and a first set of weight parameters, the first set of weight parameters determined using first confidence metrics for each of the first heart rate metric, the second heart rate metric and the third heart rate metric; and determine, for a second measurement window, a second heart rate value for the user using the received of the first and second heart rate metrics, the third heart rate metric and a second set of weight parameters, the second set of weight parameters determined using second confidence metrics for each of the first heart rate metric, the second heart rate metric and the third heart rate metric.

12. The system of claim 11, wherein the third wearable electronic device is configured to, in response to determining that a confidence metric associated with the third heart rate metric fails to satisfy a criteria:

deactivate the third heart rate sensor for the first measurement window; and determine the first heart rate value using the first heart rate metric and the second heart rate metric.

13. The system of claim 11, wherein the first wearable electronic device is configured to, for each of the first measurement window and the second measurement window:

receive the second heart rate metric from the second wearable electronic device;

compare the first heart rate metric to the second heart rate metric; and operate the first wireless communication device to transmit one of the first heart rate metric or the second heart rate metric to the third wearable electronic device based on the comparison.

14. The system of claim 13, wherein the third wearable electronic device is configured to determine the first and second heart rate values using the received one of the first heart rate metric and the second heart rate metric and the third heart rate metric for each respective measurement window.

15. The system of claim 13, wherein the first wearable electronic device is configured to, for each of the first measurement window and the second measurement window:

in response to transmitting the first heart rate metric to the third wearable electronic device, deactivate the second heart rate sensor for a subsequent measurement window; and in response to transmitting the second heart rate metric to the third wearable electronic device, deactivate the first heart rate sensor for the subsequent measurement window.

16. The system of claim 11, wherein each of the first heart rate sensor, the second heart rate sensor and the third heart rate sensor comprise an optical sensor.

17. A system for determining a heart rate of a user, the system comprising:

a first wearable electronic device comprising a first heart rate sensor and a first wireless communication device, the first wearable electronic device configured to operate the first heart rate sensor to detect a first heart rate metric at a first location on the user;

a second wearable electronic device comprising a second heart rate sensor and a second wireless communication device, the second wearable electronic device configured to operate the second heart rate sensor to detect a second heart rate metric at a second location on the user;

a third wearable electronic device comprising a third heart rate sensor and a third wireless communication device, the third wearable electronic device configured to operate the third heart rate sensor to detect a third heart rate metric at a third location on the user; and an electronic device, wherein:

for a first measurement window:

the first wearable electronic device is configured to select one of the first heart rate metric or the second heart rate metric to transmit to the electronic device based on a first comparison of confidence metrics of the first and second heart rate metrics; and the electronic device is configured to use the received one of the first heart rate metric or the second heart rate metric, and the third heart rate metric, to generate a first heart rate value for the user for the first measurement window; and for a second measurement window:

the first wearable electronic device is configured to select one of the first heart rate metric or the second heart rate metric to transmit to the electronic device based on a second comparison of the confidence metrics of the first and second heart rate metrics; and the electronic device is configured to use the received one of the first heart rate metric or the second heart rate metric, and the third heart rate metric, to generate a second heart rate value for the user for the second measurement window.

18. The system of claim 17, wherein:

the first comparison of the confidence metrics of the first and second heart rate metrics precedes the first measurement window; and the second comparison of the confidence metrics of the first and second heart rate metrics precedes the second measurement window.

19. The system of claim 18, wherein in response to selecting the first heart rate metric to transmit to the electronic device for the second measurement window, the first wearable electronic device is configured to cause the second heart rate sensor to deactivate for at least a portion of the second measurement window.

20. The system of claim 17, wherein:

in response to determining that a confidence metric associated with the third heart rate metric falls below a defined threshold for the second measurement window, the third wearable electronic device is configured to deactivate the third heart rate sensor for at least a portion of a third measurement window; and the electronic device is configured to determine a third heart rate value for the third measurement window using the first heart rate metric or the second heart rate metric selected for the third measurement window.

* * * * *